(12) United States Patent
Lv et al.

(10) Patent No.: US 10,203,293 B2
(45) Date of Patent: Feb. 12, 2019

(54) METHOD FOR LIGHTNING STROKE IDENTIFICATION AND LOCATION ON OPTICAL FIBER COMPOSITE OVERHEAD GROUND WIRE

(71) Applicants: STATE GRID CORPORATION OF CHINA CO., LTD., Beijing (CN); GLOBAL ENERGY INTERCONNECTION RESEARCH INSTITUTE, CO., LTD., Beijing (CN); STATE GRID HEBEI ELECTRIC POWER COMPANY CO., LTD., Shijiazhuang (CN)

(72) Inventors: Lidong Lv, Beijing (CN); Cheng Zhong, Beijing (CN); Fengzhen Zhou, Beijing (CN); Weiwei Miao, Beijing (CN); Yun Liang, Beijing (CN); Binglin Li, Beijing (CN); Jinghong Guo, Beijing (CN); Ningxi Song, Beijing (CN); Han Su, Beijing (CN)

(73) Assignees: STATE GRID CORPORATION OF CHINA CO., LTD., Beijing (CN); GLOBAL ENERGY INTERCONNECTION RESEARCH INSTITUTE, CO., LTD., Beijing (CN); STATE GRID HEBEI ELECTRIC POWER COMPANY CO., LTD., Shijiazhuang (CN)

( * ) Notice: Subject to any disclaimer, the term of this patent is extended or adjusted under 35 U.S.C. 154(b) by 215 days.

(21) Appl. No.: 15/124,488

(22) PCT Filed: Mar. 12, 2015

(86) PCT No.: PCT/CN2015/074095
§ 371 (c)(1),
(2) Date: Sep. 8, 2016

(87) PCT Pub. No.: WO2015/135485
PCT Pub. Date: Sep. 17, 2015

(65) Prior Publication Data
US 2017/0023504 A1    Jan. 26, 2017

(30) Foreign Application Priority Data
Mar. 12, 2014 (CN) .......................... 2014 1 0090506

(51) Int. Cl.
*G01N 25/72* (2006.01)
*G01K 11/32* (2006.01)
(Continued)

(52) U.S. Cl.
CPC ......... *G01N 25/72* (2013.01); *G01D 5/35364* (2013.01); *G01K 11/32* (2013.01); *G01M 11/30* (2013.01); *G01R 29/0842* (2013.01)

(58) Field of Classification Search
CPC .... G01N 25/72; G01D 5/35364; G01K 11/32; G01M 11/30; G01R 29/0842; G01R 29/0814; G01R 31/08; G01R 31/085
See application file for complete search history.

(56) References Cited

U.S. PATENT DOCUMENTS 4,801,937 A * 1/1989 Fernandes ............ G01R 15/142
                                                        323/357
4,821,138 A * 4/1989 Nakano ................ G01R 15/142
                                                        324/127

(Continued)

*Primary Examiner* — Lisa Caputo
*Assistant Examiner* — Philip Cotey
(74) *Attorney, Agent, or Firm* — Platinum Intellectual Property LLP

(57) ABSTRACT

The present invention discloses a method for lightning stroke identification and location on optical fiber composite (Continued)

overhead ground wire. In the method, according to the property that the lightning stroke will cause a sudden temperature rise at the lightning stroke position on the optical fiber composite overhead ground wire, optical fiber resources in the optical fiber composite overhead ground wire and the high-sensitivity detection and high-precision event locating capability of a distributed optical fiber temperature sensor can be fully utilized. The distributed optical fiber temperature sensor is connected to a spare optical fiber in the optical fiber composite overhead ground wire, and the corresponding relation between the geographical position of the optical fiber composite overhead ground wire and the distributed temperature curve is established, and then the temperature data at the same position in the temperature curve at different moments are respectively compared to extract a sudden temperature change area. In addition, the temperature change of several positions adjacent to the sudden temperature change area in the temperature curve are compared to exclude interference factors in temperature measurement, so as to determine that the sudden temperature change is caused by instant heating from an external factor, namely the lightning stroke, and finally, the lightning stroke is identified and located in combination with the change of counting data of a lightning arrester.

1 Claim, 2 Drawing Sheets

(51) Int. Cl.
*G01D 5/353* (2006.01)
*G01M 11/00* (2006.01)
*G01R 29/08* (2006.01)

(56) References Cited

U.S. PATENT DOCUMENTS

| | | | | |
|---|---|---|---|---|
| 4,904,996 | A * | 2/1990 | Fernandes | G01R 15/142 340/601 |
| 5,125,738 | A * | 6/1992 | Kawamura | G01R 31/088 250/227.14 |
| 5,138,265 | A * | 8/1992 | Kawamura | G01K 11/12 324/520 |
| 2006/0126252 | A1* | 6/2006 | Mortensen | G01W 1/16 361/118 |
| 2011/0077866 | A1* | 3/2011 | Woo | H02H 3/40 702/4 |
| 2011/0102767 | A1* | 5/2011 | Volanthen | G01R 29/0842 356/32 |
| 2013/0054183 | A1* | 2/2013 | Afzal | G01R 15/142 702/141 |
| 2014/0052393 | A1* | 2/2014 | Tang | H02G 7/20 702/59 |
| 2014/0107926 | A1* | 4/2014 | Woo | H02H 5/005 702/4 |
| 2016/0202427 | A1* | 7/2016 | Smith | G02B 6/3604 385/26 |

* cited by examiner

METHOD FOR LIGHTNING STROKE IDENTIFICATION AND LOCATION ON OPTICAL FIBER COMPOSITE OVERHEAD GROUND WIRE

FIELD OF THE INVENTION

The present invention belongs to the sensing field in power industry, and particularly relates to a method for accurately identifying and locating the lightning stroke event on the optical fiber composite overhead ground wire.

BACKGROUND OF THE INVENTION

The optical fiber composite overhead ground wire is an important line for the electric power system communications, and is responsible for power dispatching, relay protection and many other services. At present, accident potentials on the communication lines in power industry are generally investigated by manpower inspection. This inspection mode is weak in pertinence, and it cost long time to conduct a routing inspection, so it is of low efficiency. Lightning stroke, ice covering, typhoon and the like are main reasons that lead the faults of the optical fiber composite overhead ground wire, and compared with ice covering, typhoon and the like, the faults caused by the lightning stroke on the optical fiber composite overhead ground wire are more covert. This is because if the lightning stroke does not directly lead to break of the optical fiber composite overhead ground wire, strand breakage or increased local brittleness at the lightning stroke position is hard to be found by human eyes. If the lightning stroke on the optical fiber composite overhead ground wire can be identified and located in time and the automation level of power system operation and maintenance is improved, the line inspection is more targeted, so as to save human resources, money expenditure and material consumption.

Among the present technologies, the invention patent application No. 201110214109.1 discloses a method for identifying the lightning stroke and non-lightning stroke events on the power transmission line. The lightning stroke is identified by determining the fault traveling wave current and comparing wave coda time with a threshold, but the method cannot be used to accurately locate the lightning stroke position. The invention patent application No. 200610021239.2 discloses a method for determining a lightning stroke position on the power transmission line, in which a lightning stroke sensor is arranged, and a dedicated database that relates to the lightning current, the voltage induced by the lightning and the lightning stroke position is established to identify the lightning stroke event on the power transmission line. However, the aforementioned methods for identifying and locating the lightning stroke events are based on electronic sensors, which do not use any optical fiber resources in the optical fiber composite overhead ground wire. Therefore, the present invention provides a distributed optical fiber temperature sensor based method to identify and locate the lightning stroke events on the optical fiber composite overhead ground wire, which can make full use of the optical fiber resources and the high-sensitivity detection and high-precision event location capability of the distributed optical fiber temperature sensor, to monitor the temperature suddenly rising point or section along the optical fiber composite overhead ground wire in real time, and analyze temperature change processes of the suddenly rising point or section at different moments and temperature change features at positions adjacent to the temperature suddenly rising point or section, so as to accurately identify and locate the lightning stroke event.

SUMMARY OF THE INVENTION

The present invention provides a method for accurately identifying and locating lightning stroke evens on the optical fiber composite overhead ground wire. The object of the present invention is to make full use of optical fiber resources in the optical fiber composite overhead ground wire and the capability of high-sensitive temperature sensing and high-precision event locating and other properties of the distributed optical fiber temperature sensor, to capture the temperature suddenly rising point or section on a temperature curve along the optical fiber composite overhead ground wire, and analyze temperature change processes of the sudden temperature change area at different moments and temperature change features of positions adjacent to the temperature suddenly rising point or section, so as to accurately identify and locate a lightning stroke event.

Summary of the Invention for Realizing the Object of the Present Invention Includes the Following Steps:

step 1, The distributed optical fiber temperature sensor links the optical fiber in the optical fiber composite overhead ground wire, detects the temperature information along the said optical fiber composite overhead ground wire to obtain the temperature distribution curve about the optical fiber distance from the output port of the distributed optical fiber sensor and the temperature value corresponding to the fiber distance. The said temperature information along the said optical fiber composite overhead ground wire is send to a computer, and then in the said computer optical fiber distance is converted to geographic information in a map (longitude and latitude coordinates), so the temperature distribution curve with the geographical information of the said optical fiber composite overhead ground wire is established, in which the distributed temperature value corresponds to the geographical information of the said optical fiber composite overhead ground wire.

step 2, The distributed optical fiber sensor feeds back the temperature data once at a regular time interval to the said computer, and the said computer saves the temperature data, and compares the said temperature data with several temperature data measured before to find whether the temperature data at the same geographical position has suddenly temperature rising point or section. If there is a temperature suddenly rising point or section, the position of the said temperature suddenly rising point or section is located. And then the lightning stoke event is identified by analyzing the temperature change trend of the said temperature suddenly rising points or section in the next several successive measurements.

step 3, Several positions adjacent to the temperature suddenly rising point or section are selected to compare whether the temperature data at the said positions have temperature suddenly rising phenomenon in the several successive measurements. And if the temperature data at these positions do not have temperature suddenly rising phenomenon in the several successive measurements, it is determined that the previously captured temperature suddenly rising point or section is heated by external heat transfer.

step 4, The temperature change trend at the geographical position that corresponds to the temperature suddenly rising point or section of the optical fiber composite overhead ground wire is analyzed with the data in the several successive measurements. If the temperature at the temperature suddenly rising point or section is the same with the temperatures at the several positions adjacent positions after several successive measurement time intervals, the said temperature suddenly rising point or section is confirmed to be caused by heat transfer in the lightning stroke, and then the lightning stroke position on the optical fiber composite overhead ground wire in the geographical information system is determined, and then is marked in a map.

Preferably, the distributed optical fiber temperature sensor is a Raman optical time domain reflectometer;

preferably, the distributed optical fiber temperature sensor is a Brillouin optical time domain reflectometer;

preferably, the distributed optical fiber temperature sensor is a Brillouin optical time domain analyzer;

preferably, the change of the number of lightning stroke recorded by the lightning arrester is used as a reference for identifying the lightning stroke in the method;

preferably, the time interval of the distributed optical fiber temperature sensor for measuring the temperature along the optical fiber composite overhead ground wire is less than 5 min;

preferably, the spatial resolution of the distributed optical fiber temperature sensor is smaller than 2 m;

preferably, when the temperature rise value of a certain point or section along the optical fiber composite overhead ground wire is larger than the temperature measurement precision value of the adopted distributed optical fiber temperature sensor, it is determined that the area has a sudden temperature change; and preferably, the several positions adjacent to the sudden temperature rising point or section are positions of two points in front of and two points behind the sudden temperature change position.

Compared with the Closest Prior Art, the Present Invention has the Following Beneficial Effects:

The optical fiber resources in the optical fiber composite overhead ground wire and the high-sensitivity temperature sensing and high-precision event locating and other properties of the distributed optical fiber temperature sensor are fully used to accurately identify and locate the lightning stroke events. The distributed optical fiber temperature sensor can realize non-blind zone monitoring along the entire optical fiber line. Compared with the point type sensor, the distributed optical fiber temperature sensor can greatly reduce the number of sensors, so as to save the cost, and moreover, the distributed optical fiber temperature sensor has better practical value due to the properties of passiveness, electromagnetic immunity and the like. The present invention is of significance to improve the automation level of the power system, which saves human, financial and material resources for power operation and maintenance.

BRIEF DESCRIPTION OF THE DRAWINGS

The present invention will be hereafter be described with reference to the accompanying drawings.

DETAILED DESCRIPTION OF THE EMBODIMENTS

Technical solutions in the embodiments of the present application will be clearly and fully described below in combination with the accompanying drawings.

Figure 1:
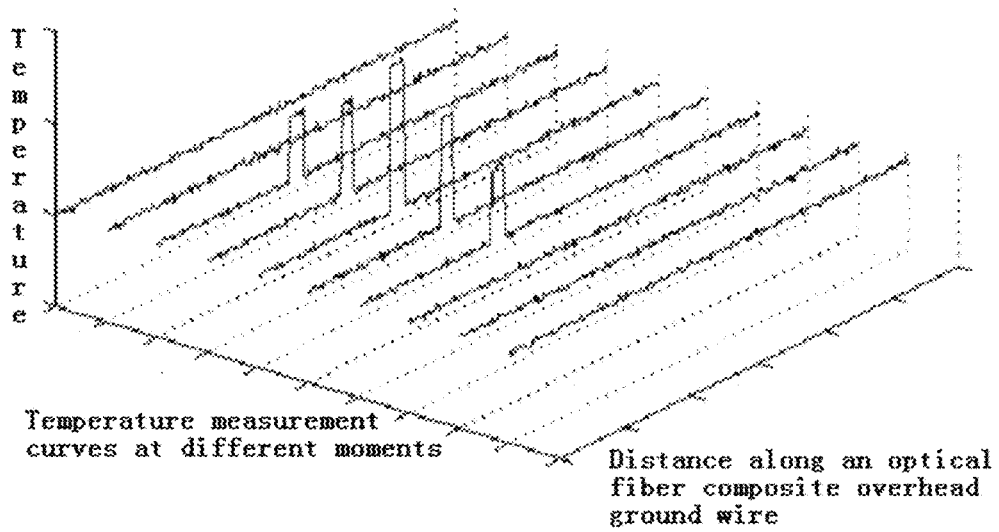
FIG. 1 is a schematic illustration of the temperature change process at the lightning stroke position on the optical fiber composite overhead ground wire.

FIG. 1 shows a temperature change process at the lightning stroke position on the optical fiber composite overhead ground wire. Since optical fibers in the optical fiber composite overhead ground wire are packaged in a steel pipe, and moreover, waterproof ointment filled in gaps of aluminum wires wrapped outside of the steel pipe has heat insulation property, the temperature at the lightning stroke position on the optical fiber composite overhead ground wire will rise gradually, and finally, the temperature at the lightning stroke position gradually recovers to be the same with the temperature of other areas adjacent to the lightning stroke position due to heat dissipation.

The present invention makes full use of optical fiber resources in the optical fiber composite overhead ground wire and high-sensitivity temperature sensing and high-precision event locating and other properties of a distributed optical fiber temperature sensor. Based on the obtained temperature data it captures the temperature suddenly rising point or section on the optical fiber composite overhead ground wire, and analyzes temperature change trends at the temperature suddenly rising point or section at different moments and the temperature change trends at the positions adjacent to the temperature suddenly rising point or section, so as to accurately identify and locate the lightning stroke events. By experiments, we found that lightning stroke will not make the position attacked appear very high temperature increase, because of the heat insulation property of the ointment in the optical fiber composite overhead ground wire. But the temperature sensed by the distributed optical fiber temperature sensors rises first and then decreases in several minutes after the lightning stroke event. So the temperature change trend in a short time after the temperature suddenly rising can be used to judge whether it is the lightning stroke event. Due to the problem of grounding mode of optical fiber composite overhead ground wire, the inductive electricity from the phase lines may cause the said optical fiber composite overhead ground wire to warm up somewhere and even fuses it. In this condition, the temperature rising process is relatively long and will not decrease generally. Fire will also cause the temperature change, but it usually happens in many separate positions along the optical fiber composite overhead ground wire, and duration time is also relatively long. The weather change may lead temperature suddenly rising, but the temperature rising zone is relatively long, which is generally longer than 100 meters, while the zone attacked by lightning is commonly less than 10 centimeters. Therefore, by comparison of the temperature change characteristics at the temperature rising point or section and its adjacent positions in successive measurements, the lightning stroke event can be identified and located.

Figure 2:
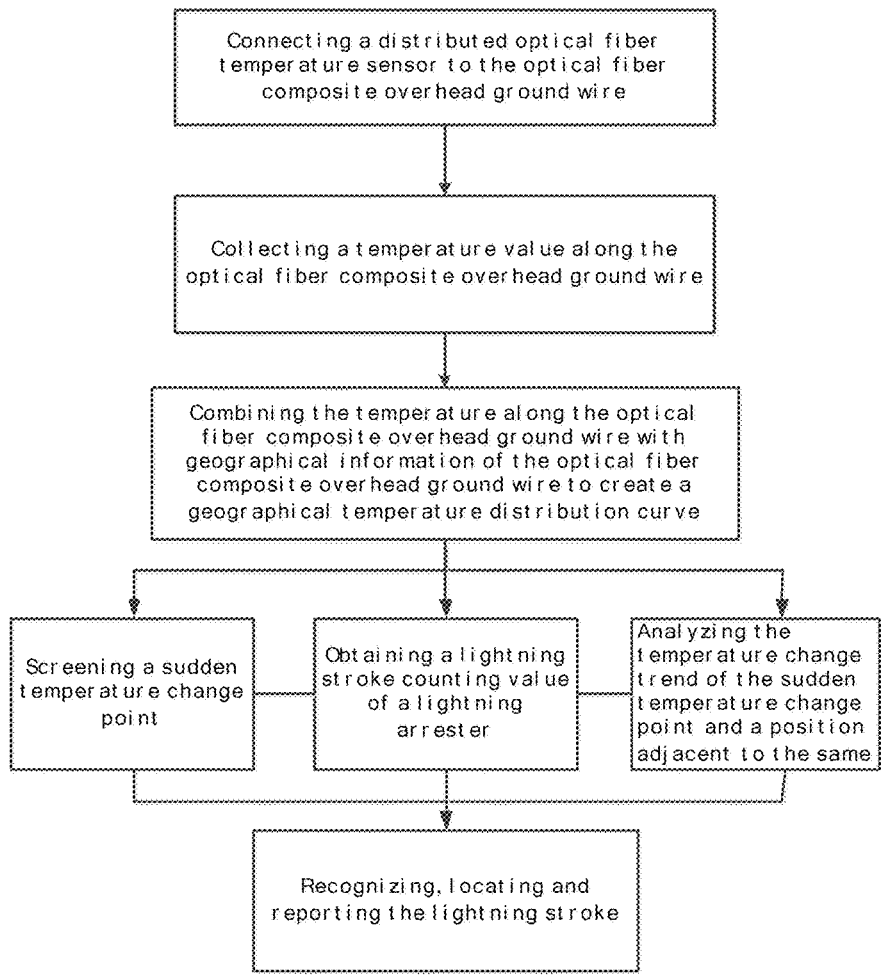
FIG. 2 is a flowchart of a method for identifying and locating the lightning stroke events on the optical fiber composite overhead ground wire provided by the present invention.

FIG. 2 shows a flowchart of a method for identifying and locating lightning stroke on the optical fiber composite overhead ground wire in the embodiment, comprising the following specific steps:

step 1, The distributed optical fiber temperature sensor links the spare optical fiber in the optical fiber composite overhead ground wire, detects the temperature information along the wire, and establishes the geographical temperature distribution curve in which the distributed temperature corresponds to the geographical information of the optical fiber composite overhead ground wire.

step 2, The distributed optical fiber sensor feeds back the temperature data once at a regular time interval, and compares the temperature data with several temperature data measured before to find whether the temperature data at the same geographical position has a sudden change, and then determines the position of a sudden change area, and analyzes the change trend of temperatures at the sudden temperature change area in several successive measurements.

step 3, Several positions adjacent to the sudden temperature change area are selected to compare whether the temperatures at these positions have sudden changes in the several successive measurements And if the temperatures at these positions do not have sudden changes in the several successive measurements, it is determined that the previously captured sudden temperature change area is caused by external heat transfer.

step 4, The temperature change trend at the geographical position of the optical fiber composite overhead ground wire that corresponds to the sudden temperature change area is analyzed in the several successive measurements. If the temperature at the sudden change area is the same with the temperatures at the several positions adjacent to the sudden change area after several measurement time intervals, the sudden temperature change in the area is confirmed to be generated by heat transfer in the lightning stroke, and then the lightning stroke position on the optical fiber composite overhead ground wire in the geographical information system is determined.

The distributed optical fiber temperature sensor includes a Raman optical time domain reflectometer, a Brillouin optical time domain reflectometer, or a Brillouin optical time domain analyzer. The measurement time interval of the distributed optical fiber temperature sensor for measuring the temperature along the optical fiber composite overhead ground wire is less than 5 min, and the spatial resolution of the distributed optical fiber temperature sensor is smaller than 2 m.

The change of the number of lightning stroke recorded by the lightning arrester is used as a reference for identifying the lightning stroke in the method. When the temperature rise value of a certain area along the optical fiber composite overhead ground wire is larger than the temperature measurement precision of the distributed optical fiber temperature sensor, it is determined that the area has a sudden temperature change, and the several positions adjacent to the sudden temperature change area are positions of two points in front of and two points behind the sudden temperature change position.

Figure 3:
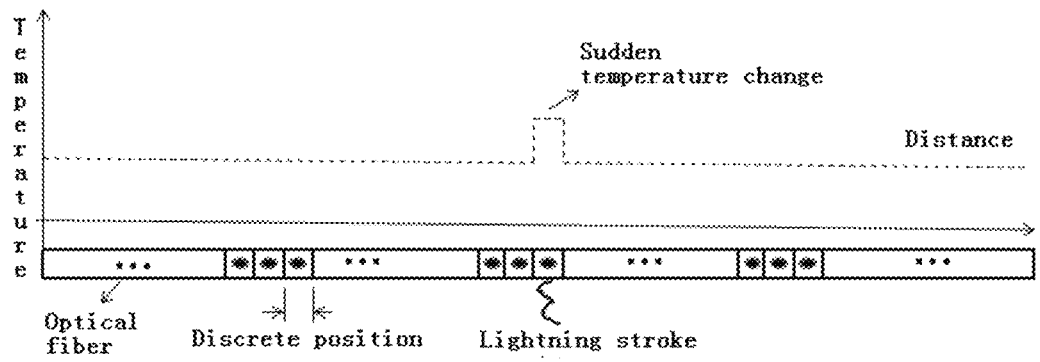
FIG. 3 is a schematic illustration of a corresponding relation of optical fiber sensing unit division and the temperature curve along the optical fiber composite overhead ground wire in an embodiment of the present invention.

In the embodiment, the Brillouin optical time domain reflectometer is connected to the spare optical fiber in the optical fiber composite overhead ground wire. The data sampling rate of the Brillouin optical time domain reflectometer is 100 Msps, so that the temperature data points are distributed every 0.1 m along the optical fiber. Meanwhile, the spatial resolution of the Brillouin optical time domain reflectometer is set to 1 m, which means that the minimal distinguishable distance of the measured temperature data is 1 m. Minimal distinguishable units and the distributed temperature data captured are shown in FIG. 3.

Figure 4:
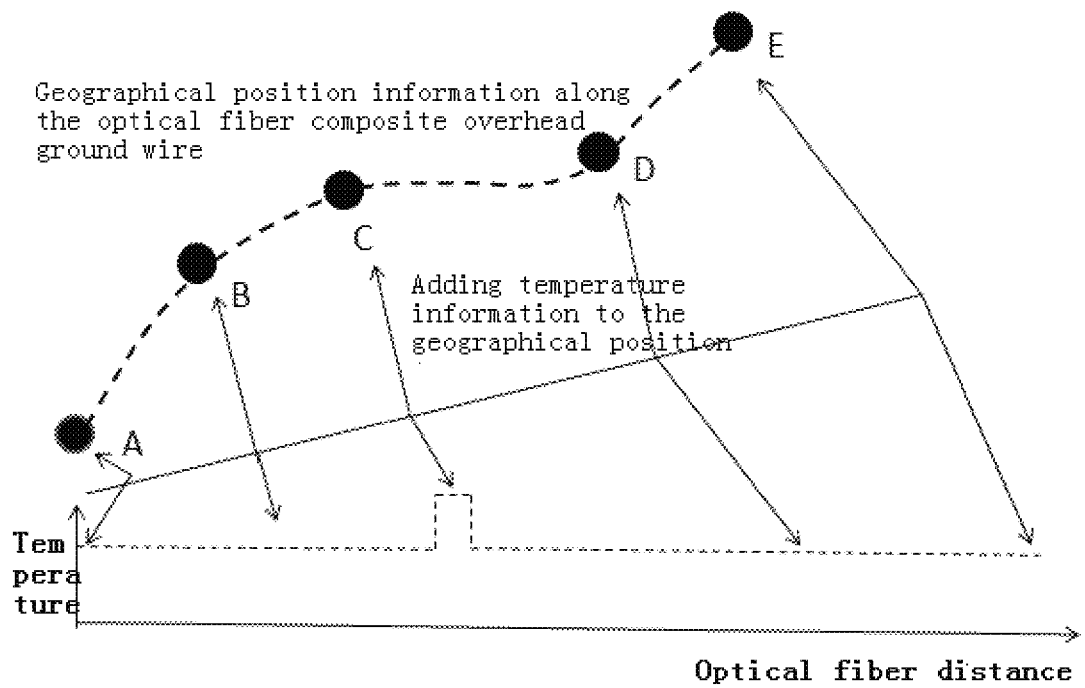
FIG. 4 is a mapping graph between temperature distribution along the optical fiber composite overhead ground wire and a geographical information system in an embodiment of the present invention.

The temperature distribution curve corresponding to the geographical information system of the optical fiber composite overhead ground wire is established as shown in FIG. 4, so as to accurately find out the corresponding geographical position from any temperature data point. The Brillouin optical time domain reflectometer feeds back the temperature data once every 3 min and then compares the temperature data with several temperature data measured before.

If the sudden temperature change occurs, the temperature curve after the data subtraction processing will display the temperature rise area, as shown in FIG. 1. The sudden temperature change is defined as that the sudden temperature rise value of a certain position is larger than the measurement precision of the distributed temperature sensor. And then the temperature data obtained in different measurement time points at the same geographical position are compared to find out whether it has a sudden temperature change. And then the position of the sudden temperature change area is captured, and the change trend of the temperature at this position in several successive measurements is determined;

Several positions adjacent to the sudden temperature change area are selected to compare whether the temperature data in the several successive measurements at these positions have sudden changes, and if sudden temperature change does not occur, as shown in FIG. 1 the temperature at the position near the sudden temperature change area has no obvious change, then it can be determined that the previously captured sudden temperature change area is heated by external heat transfer.

The temperature change trend of the optical fiber composite overhead ground wire at the sudden temperature change area in the several successive measurements is analyzed. If it is found that the temperature of the sudden temperature change area recovers to the same with the temperatures at the several positions adjacent to the sudden temperature change area after several measurement time intervals, according to the sudden temperature change area and the temperature change rule of the adjacent areas at different measurement moments as shown in FIG. 1 and in combination with the change of counting data of the lightning arrester; it is confirmed that the sudden temperature change in this area is generated by the heat transfer of lightning stroke, And then the lightning stroke position in the geographical information system of the optical fiber composite overhead ground wire is determined, the lightning stroke position in the geographical information system containing temperature information of the optical fiber composite overhead ground wire is marked and reported as an alarm Finally it should be noted that the described embodiments are merely a part, but not all, of the embodiments of the present invention. Based on the embodiments of the present invention, all of other embodiments obtained by those of ordinary skill without any creative effort are within the protection scope of the present application.

What is claimed is:

1. A method for lightning stroke identification and location on an optical fiber composite overhead ground wire, comprising the following steps:

step 1, a distributed optical fiber temperature sensor links a spare optical fiber in the optical fiber composite overhead ground wire, and detects the temperature along the said optical fiber composite overhead ground wire to obtain the temperature distribution curve about the optical fiber distance from the output port of the said distributed optical fiber temperature sensor and the temperature value corresponding to the fiber distance;

wherein the spatial resolution of the said distributed optical fiber temperature sensor is smaller than 2 m;

wherein the said distributed optical fiber temperature sensor is one of a Raman optical time domain reflectometer; a Brillouin optical time domain reflectometer; or a Brillouin optical time domain analyzer;

the said temperature information along the said optical fiber composite overhead ground wire obtained by the said distributed optical fiber temperature sensor is sent to a computer, and then in the said computer optical fiber distance is converted to geographic information in a map longitude and latitude coordinates, so the temperature distribution curve with the geographical information of the said optical fiber composite overhead ground wire is established, in which the distributed temperature value corresponds to the geographical information of the said optical fiber composite overhead ground wire;

step 2, the said distributed optical fiber sensor feeds back the temperature data once at a regular time interval to the said computer, and the said computer saves the temperature data, and compares the temperature data with several temperature data measured before to find whether the temperature data at the same geographical position has a temperature suddenly rising point or section;

wherein once a temperature rising value of a certain position or section along the said optical fiber composite overhead ground wire is larger than 2 degrees Celsius, this position or section is determined as the temperature suddenly rising position or section;

wherein the said regular time interval is less than 5 minutes;

wherein at each position distributed along the said optical fiber composite overhead ground wire the temperature data of it in 5 successive measurements are adopted for comparison to determine the temperature suddenly rising position or section;

and then the temperature change trend of the said temperature suddenly rising point or section in the next 5 successive measurements are extracted for analyzing; if in the said next 5 successive measurements, the temperature value at the located temperature suddenly rising point or section becomes the same with the temperature values at the adjacent positions, and the located temperature suddenly rising point or section is marked as an objective position;

step 3, two adjacent positions in front and two adjacent positions behind of the objective position are selected to compare whether the temperature data at the said 5 positions have similar temperature suddenly rising phenomenon; if in the said 5 positions, there are more than one objective positions, it is determined that the previously captured temperature suddenly rising phenomenon at the said objective positions are not caused by lightning stroke;

if in the said 5 positions, there is only one objective position, the objective position is identified as the position attacked by lightning stroke; wherein the change of the lightning stroke counting data of a lightning arrester is used as a reference for identifying the lightning stroke in the method; and step 4, the lightning stroke position on the said optical fiber composite overhead ground wire in the said map about the geographical information is determined, and then is marked in the said map.

* * * * *